United States Patent
Li et al.

(10) Patent No.: US 10,898,154 B2
(45) Date of Patent: Jan. 26, 2021

(54) SYSTEM AND METHOD FOR X-RAY IMAGING

(71) Applicant: SHANGHAI UNITED IMAGING HEALTHCARE CO., LTD., Shanghai (CN)

(72) Inventors: Gui Li, Shanghai (CN); Lu Xu, Shanghai (CN); Hongcheng Yang, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 896 days.

(21) Appl. No.: 15/361,036

(22) Filed: Nov. 24, 2016

(65) Prior Publication Data
US 2017/0151444 A1  Jun. 1, 2017

(30) Foreign Application Priority Data
Nov. 26, 2015  (CN) .......................... 2015 1 0836614

(51) Int. Cl.
*A61B 6/00* (2006.01)
*A61B 6/06* (2006.01)
(Continued)

(52) U.S. Cl.
CPC .............. *A61B 6/5282* (2013.01); *A61B 6/06* (2013.01); *A61N 5/1049* (2013.01); *G06T 5/50* (2013.01);
(Continued)

(58) Field of Classification Search
CPC ................ A61N 5/1045; A61N 5/1049; A61N 2005/1054; A61N 2005/1095; A61B 6/03;
(Continued)

(56) References Cited

U.S. PATENT DOCUMENTS 5,841,828 A * 11/1998 Gordon ................. G06T 11/003
378/4
7,463,712 B2 12/2008 Zhu et al.
(Continued)

FOREIGN PATENT DOCUMENTS

CN 104783819 A 7/2015

OTHER PUBLICATIONS

First Office Action for Chinese Application No. 201510836614.8 dated Nov. 11, 2016, 7 pages.

*Primary Examiner* — Anastasia Midkiff
(74) *Attorney, Agent, or Firm* — Metis IP LLC

(57) ABSTRACT

The present disclosure provides a system and method for X-ray imaging. The method of calculating scatter in an X-ray image may include forming a modulated X-ray image. The method of forming the modulated X-ray image may include acquiring X-rays through a collimator module and an imaged object in sequence to generate an X-ray image group; the acquisition may be performed during a movement of the collimator module in a first direction and the X-ray image group may include a plurality of X-ray images acquired at different times during the movement of the collimator; extracting sub-zones from the plurality of X-ray images in the X-ray image group; combining the sub-zones in the first direction to form the modulated X-ray image. In the present disclosure, an intensity distribution of the X-rays may be adjusted flexibly using a collimator without adding any extra hardware. In addition, scatter components in the X-ray images may be calculated to eliminate the scatter in the X-ray images finally.

20 Claims, 12 Drawing Sheets

(51) Int. Cl.
*G06T 5/50* (2006.01)
*A61N 5/10* (2006.01)
*G21K 1/04* (2006.01)
*G06T 5/00* (2006.01)

(52) U.S. Cl.
CPC ........... *A61B 6/4035* (2013.01); *A61B 6/5205* (2013.01); *A61B 6/54* (2013.01); *A61N 5/1045* (2013.01); *A61N 2005/1095* (2013.01); *G06T 5/001* (2013.01); *G06T 2207/20212* (2013.01); *G06T 2207/20224* (2013.01); *G21K 1/043* (2013.01)

(58) Field of Classification Search
CPC ....... A61B 6/06; A61B 6/4035; A61B 6/5205; A61B 6/5282; A61B 6/54; G06T 5/001; G06T 5/50; G06T 7/0012; G06T 2207/10116; G06T 2207/20224; G06T 2207/20212; G21K 1/043
See application file for complete search history.

(56) References Cited

U.S. PATENT DOCUMENTS

| | | | |
|---|---|---|---|
| 8,199,874 B2 | 6/2012 | Toth et al. | |
| 8,867,699 B2 * | 10/2014 | Mori | A61B 6/06 378/2 |
| 8,897,413 B2 | 11/2014 | Heuscher | |
| 2007/0268997 A1 | 11/2007 | Zhu et al. | |
| 2014/0146935 A1 * | 5/2014 | Goldammer | A61B 6/4035 378/7 |

* cited by examiner

SYSTEM AND METHOD FOR X-RAY IMAGING

The application claims priority of Chinese Patent Application No. 201510836614.8 filed on Nov. 26, 2015, the entire contents of which are hereby incorporated by reference.

TECHNICAL FIELD

This application generally relates to medical imaging, and more specifically, relates to a system and method for X-ray image forming, scatter calculating, and X-ray image reconstruction.

BACKGROUND

In X-ray imaging, scatter may be a primary cause for image quality deterioration. Specifically, for an X-ray system with a large area detector, such as a radiotherapy system used for cone beam CT, an EPID (Electronic Portal Imaging Device) may be used to receive the X-rays in which the scattered rays account for a large proportion. The scattered rays may cause cup artifacts in images, which may contribute to a decline of contrast and accuracy in the images. During the radiotherapy, real-time images of a patient may be obtained through the cone beam CT, which may be used to guide the radiotherapy treatment. Position errors of the radiotherapy treatment may be generated because of the decline of the image accuracy, so precise radiotherapy of tumor can't be achieved.

Two main approaches have been proposed to correct scatter in images. One approach may be hardware-based methods, which suppress or correct the scatter by adding a number of hardware tools to an X-ray imaging system to reduce the amount of the scattered rays which reach the detector. The common hardware tools for correcting the scatter may include an X-ray collimator, an anti-scatter grid, etc. The other approach may be software-based methods, which correct the scatter in the X-ray images based on the scatter distribution obtained by analyzing the projection images and estimating the scatter based on an imaged object.

SUMMARY

The present disclosure relates to X-ray imaging. A first aspect of the present disclosure relates to a method of calculating scatter in an X-ray image. The method may include forming a modulated X-ray image. The method of forming the modulated X-ray image may include acquiring X-rays through a collimator module and an imaged object in sequence to generate an X-ray image group; wherein the acquisition may be performed during a movement of the collimator module in a first direction, and wherein the X-ray image group may include a plurality of X-ray images acquired at different times during the movement of the collimator module; extracting sub-zones from the plurality of X-ray images in the X-ray image group; and combining the sub-zones in the first direction to form the modulated X-ray image.

In some embodiments, the acquisition frequency for obtaining the X-ray image group is proportional to a speed of movement of the collimator module.

In some embodiments, the collimator module may be a multi-leaf collimator including a group of leaves. The group of leaves may be equal in length and may move together in the first direction.

A second aspect of the present disclosure relates to another method of calculating scatter in an X-ray image. The method may include forming a modulated X-ray image. The method of forming the modulated X-ray image may include acquiring X-rays through a collimator module and an imaged object in sequence to generate an X-ray image group of a plurality of X-ray images; wherein the acquisition may be performed during a movement of the collimator module in a first direction; and wherein the collimator module may comprise a pair of collimators arranged with a distance in the first direction and during the movement of the collimator module, the pair of collimators may keep the distance and move at a periodic speed. In some embodiments, the periodic speed may be at least one of a periodic increased speed or a periodic decreased speed.

A third aspect of the present disclosure relates to a method of calculating scatter in a modulated X-ray image. The method may include: obtaining a modulated X-ray image using the method of forming a modulated X-ray image; low-pass filtering the modulated X-ray image to obtain a combination of a low-frequency portion of the modulated X-ray image and scatter components of the modulated X-ray image; high-pass filtering the modulated X-ray image to obtain a high-frequency portion of the modulated X-ray image; calculating an estimate of the low-frequency portion of the modulated X-ray image after the high-frequency portion are demodulated and weighted; and calculating the scatter components by subtracting the estimate of the low-frequency portion of the modulated X-ray image from the combination of the low-frequency portion and the scatter components of the low-pass filtered modulated X-ray image.

A fourth aspect of the present disclosure relates to a method of X-ray image reconstruction. The method may include: acquiring X-ray projection images of an imaged object from different projection angles; calculating scatter components of the projection images; obtaining at least one reconstructed image by reconstructing the projection images from which the scatter components are subtracted. The method of calculating the scatter components of the projection images may include: low-pass filtering a modulated X-ray image to obtain a combination of a low-frequency portion of the modulated X-ray image and scatter components of the modulated X-ray image; high-pass filtering the modulated X-ray image to obtain a high-frequency portion of the modulated X-ray image; calculating an estimate of the low-frequency portion of the modulated X-ray image after the high-frequency portion is demodulated and weighted; and calculating the scatter components by subtracting the estimate of the low-frequency portion of the modulated X-ray image from the combination of the low-frequency portion and the scatter components of the low-pass filtered modulated X-ray image.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
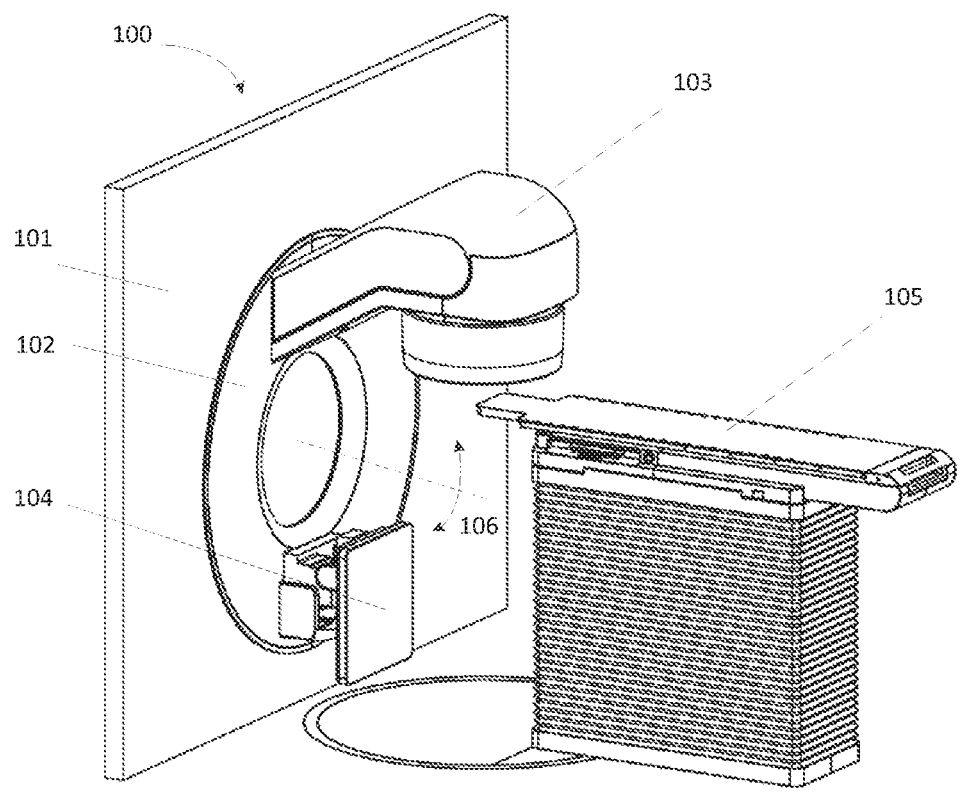
FIG. 1 is a diagram illustrating a structure of an exemplary radiotherapy system.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "unit," "module," and/or "block" used herein are one method to distinguish different components, elements, parts, section or assembly of different level in ascending order. However, the terms may be displaced by other expression if they may achieve the same purpose.

It will be understood that when a unit, engine, module or block is referred to as being "on," "connected to" or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

The present disclosure provided herein relates to a system and method for X-ray imaging. More particularly, the present disclosure relates to a method of forming a modulated X-ray image. According to some embodiments of the present disclosure, the method of forming a modulated X-ray image includes acquiring X-rays through a collimator module and an imaged object in sequence to generate an X-ray image group of a plurality of X-ray images; extracting sub-zones from the plurality of X-ray images in the X-ray image group; and combining the sub-zones to form a modulated X-ray image. In some embodiments, the acquisition may be performed during a movement of the collimator module in a first direction. In some embodiments, the X-ray image group may be a group of X-ray images acquired at different times of the movement of the collimator.

FIG. 1 is a diagram illustrating a structure of an exemplary radiotherapy system 100. As shown in FIG. 1, radiotherapy system 100 may include a fixed part 101 and a rotation part 102. Rotation part 102 may be installed on fixed part 101. Rotation part 101 may rotate around central axis 106 to treat patients from different angles.

A treatment head 103 may be installed on one side of rotation part 102. Rotation part 102 may generate high energy X-rays (e.g., million electron volt level) for radiotherapy treatment of a patient on table 105. For a same-source double-energy radiotherapy system that can output a first beam at a first energy level and a second beam at a second energy level, treatment head 103 may generate low energy X-ray (e.g., kilovolt level) for imaging a patient and images of the patient may be used to guide the radiotherapy treatment (Image Guided Radiation Therapy).

When imaging using low energy X-rays, treatment head 103 may output a cone beam. An EPID (electronic portal imaging device) 104 installed on the other side of rotation part 102 may receive X-rays through a patient so that a projection image may be obtained. If treatment head 103 outputs X-rays from different angles, projection images from different angles may be obtained. A CT (computed tomography) image of the patient may be reconstructed based on the projection images from different angles.

Figure 2:
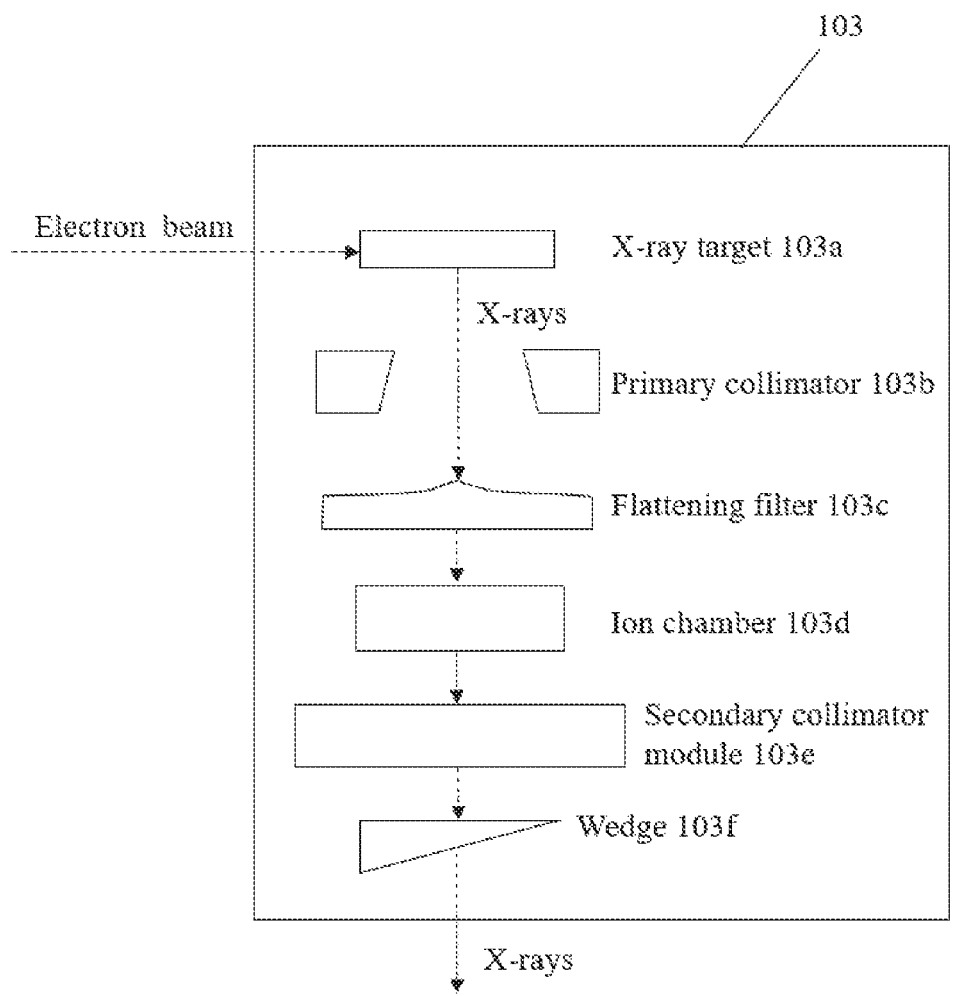
FIG. 2 is a diagram illustrating a structure of a treatment head of an exemplary radiotherapy system.

FIG. 2 is a diagram illustrating a structure of treatment head 103 of an exemplary radiotherapy system 100. As shown in FIG. 2, treatment head 103 may include an X-ray target 103a, a primary collimator 103b, a flattening filter 103c, an ion chamber 103d, a secondary collimator module 103e, and a wedge 103f. An electron beam may exit from a linear accelerator (not shown in FIG. 2). The electron beam may impinge on an X-ray target 103a and generate X-rays. Primary collimator 103b may limit the direction and the scope of the X-rays. Flattening filter 103c may flatten the X-rays. Ion chamber 103d may measure energy of the X-rays. Secondary collimator module 103e may adjust the intensity and/or shape of the X-rays. Wedge 103f may adjust the energy distribution of the X-rays. And then the X-rays may be emitted from an exit of treatment head 103.

Figure 3:
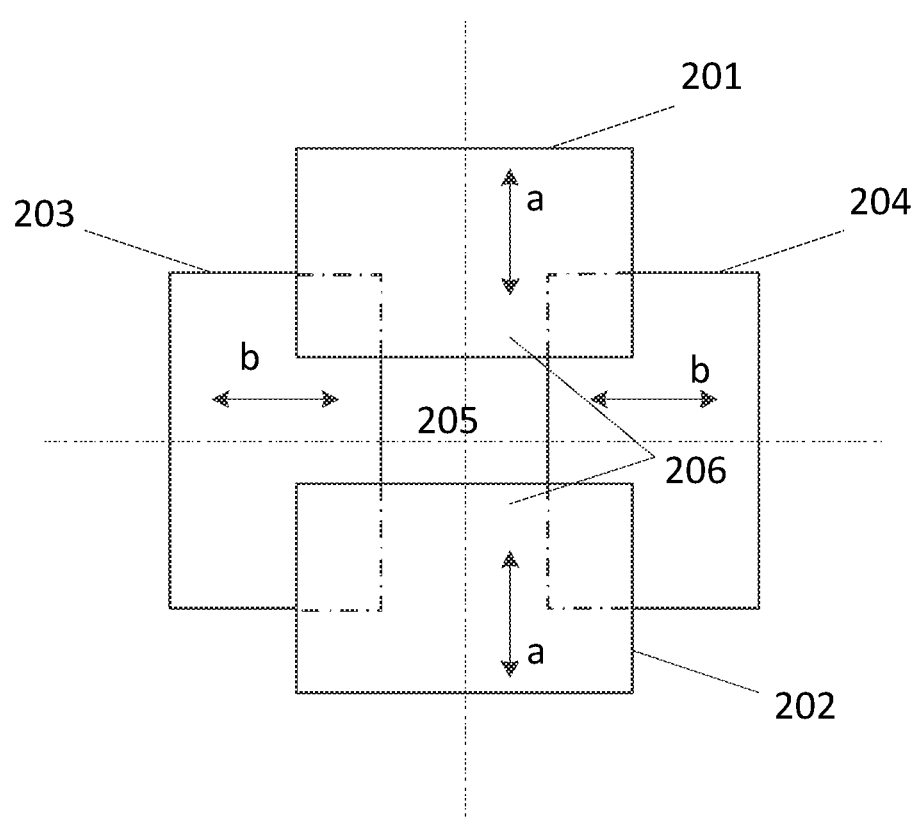
FIG. 3 is a diagram illustrating a structure of a secondary collimator module in a treatment head of an exemplary radiotherapy system.

FIG. 3 is a diagram illustrating a structure of a secondary collimator module 103e in an emitting direction of X-rays. With reference to FIG. 3, secondary collimator module 103e may include two secondary collimator units. The secondary collimator unit may include a pair of secondary collimators (e.g., secondary collimator 201 and 202, secondary collimator 203 and 204) relatively arranged in a certain direction. The X-rays may pass through region 205 without blocking or passing through the region covered by secondary collimator module 103e with decay in strength. One pair of secondary collimators 201 and 202 may be relatively arranged and driven by motors to move in direction "a." The other pair of secondary collimators 203 and 204 may be relatively arranged and driven to move in direction "b."

Figure 4:
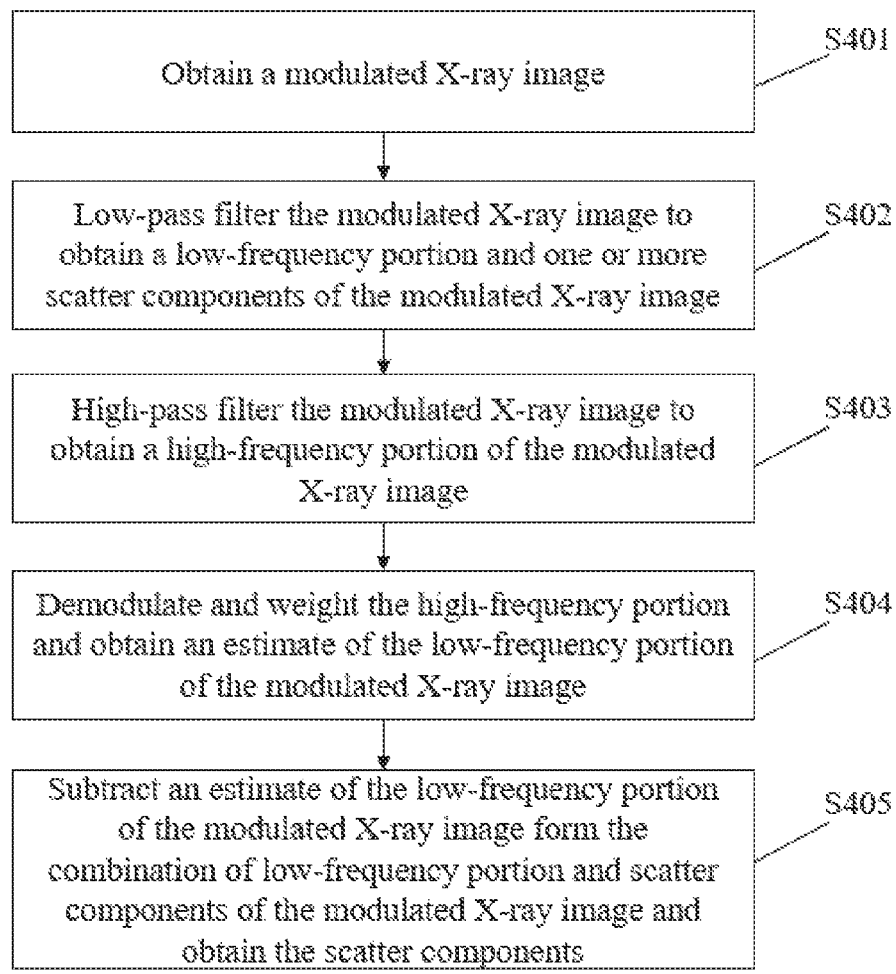
FIG. 4 is a flowchart illustrating a method of calculating scatter in X-ray images.

In conjunction with the structures described above, a method of computing scatter in an X-ray image may be illustrated as follows. As shown in FIG. 4, the method may include the following steps.

In S401, a modulated X-ray image may be obtained.

Figure 5A:
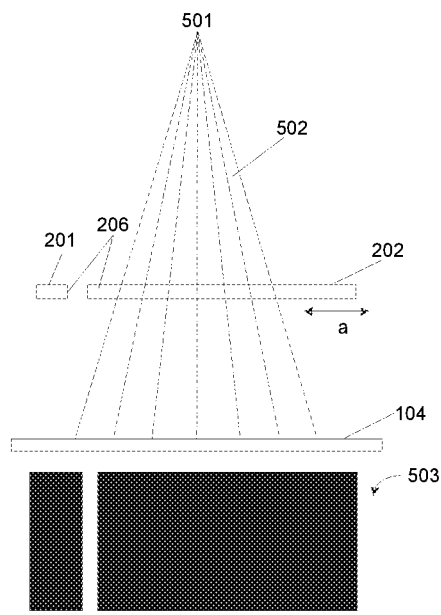
FIGS. 5a-5d are diagrams illustrating states of movement of a secondary collimator module.

A method of obtaining a modulated X-ray image may be described in connection with FIGS. 5a-5d and FIGS. 6a-6b. FIG. 5a is a diagram illustrating imaging with X-rays. X-rays 502 may be generated by an X-ray source 501. In some embodiments, the X-ray source may be an X-ray target. Before X-rays 502 pass through an imaged object (not shown in FIG. 5a, usually a patient, animals or a phantom), the intensity distribution of X-rays 502 may be modulated by secondary collimator 201 and 202 moving in a direction (e.g., direction "a" as illustrated in FIG. 3). The emitting direction of X-rays 502 may be approximately perpendicular to the direction "a." Because of divergence of X-rays 502, it is not necessary that the emitting direction of X-rays 502 is completely perpendicular to the direction in which secondary collimators 201 and 202 move.

Figure 5B:
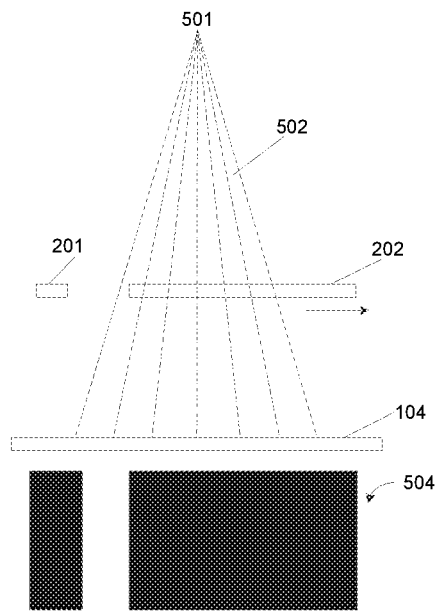

In some embodiments, as shown in FIGS. 5a and 5b, secondary collimator module 103e may include two secondary collimator units. One secondary collimator unit of secondary collimators 203 and 204 may be completely open. As used herein, completely open may mean that a field formed by secondary collimators 203 and 204 may be large enough so that secondary collimator 203 and 204 won't block the X-rays on the emitting path of the X-rays. In the other secondary collimator unit of secondary collimators 201 and 202, secondary collimator 201 may be completely open and secondary collimator 202 may move far away from secondary collimator 201 in direction "a."

As shown in FIG. 5a, X-ray image 503 may be formed on EPID 104. Black regions in X-ray image 503 may indicate that the intensity of these regions of X-ray image 503 is low due to occlusion of X-rays 502 by secondary collimator module 103e may block. White region(s) in X-ray image 503 may indicate that the intensity of the region(s) of X-ray image 503 is relatively high because secondary collimator module 103e does not block X-rays 502. Because the section of secondary collimator end 206 (shown in FIG. 3) may be rectangle, only one narrow bright stripe may be formed in X-ray image 503.

When secondary collimator 202 moves to position shown in FIG. 5b, X-ray image 504 may be formed on EPID 104. Because secondary collimator 202 has moved some distance, the width of stripes in X-ray image 504 may increase.

To generate a final X-ray image, during a movement of secondary collimator 202 in the direction "a" (also referred to as "a first direction"), a number of X-ray images may be acquired and may form an X-ray image group. The X-ray images of the X-ray image group may be acquired at different times during the movement of secondary collimator 202. In the X-ray image, a sub-zone may be extracted. The sub-zone may be near to an edge of the moving secondary collimator 202. The sub-zone may include a bright stripe and a dark stripe. For example, sub-zone 601 extracted from X-ray image 503 may include a bright stripe 6011 and a dark stripe 6012. As another example, sub-zone 602 may be extracted from X-ray image 504. Sub-zones 601, 602, 603, etc. may be combined in the direction "a" and final X-ray image 600 may be obtained. Final X-ray image 600 may display bright stripes and dark stripes which may be modulated by the movement of the collimator and an image processing method based on the ordinary X-ray images to compute the scatter in the images. Final X-ray image 600 may be referred to as the modulated X-ray image 600.

Acquisition frequency of the X-ray image group may be determined based on a speed of movement of the collimator, the width of the detector and a spacing between the bright and dark stripes in modulated X-ray image 600. The acquisition frequency is proportional to the speed of the movement of the collimator. The faster the collimator moves, the higher the acquisition frequency is.

Figure 5C:
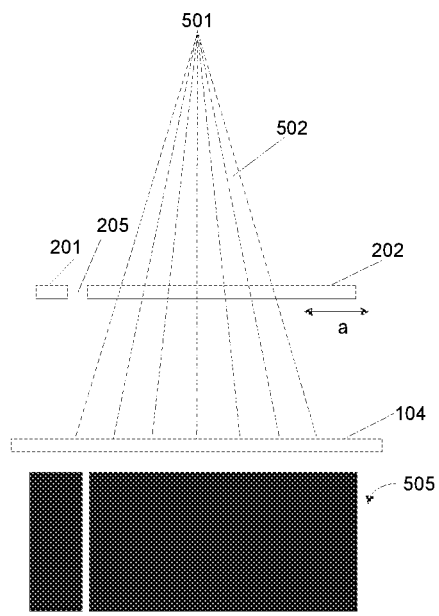
Figure 5D:
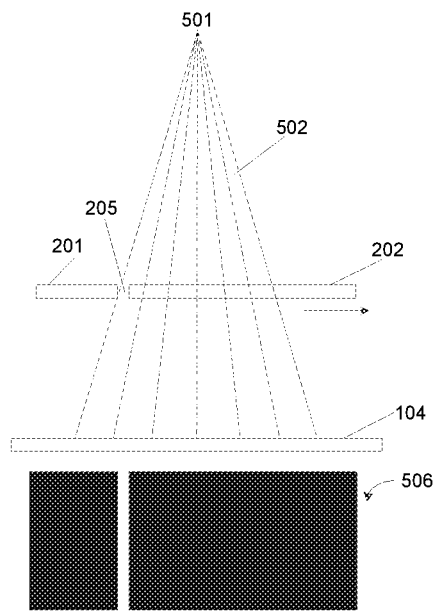
Figure 6A:
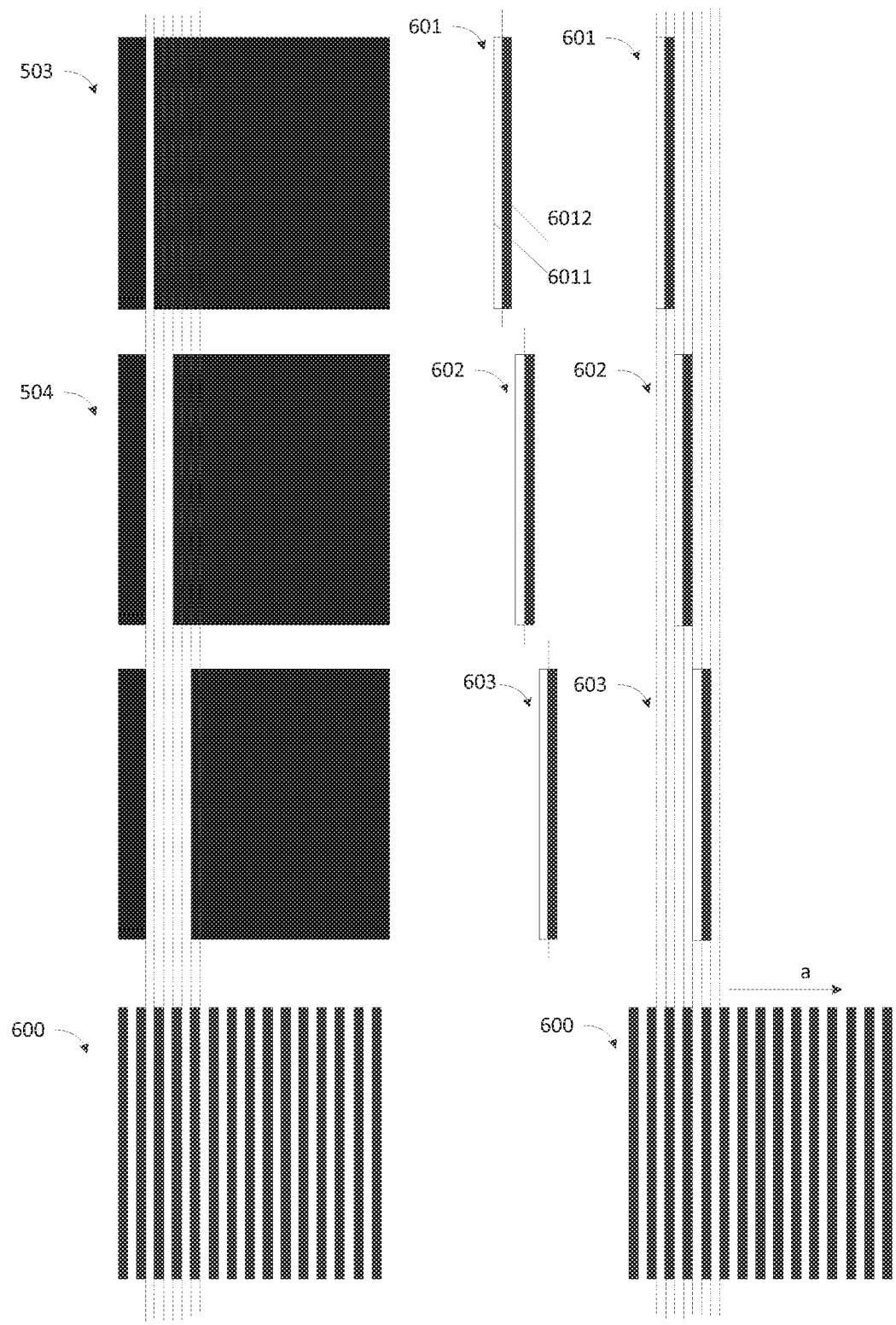
FIGS. 6a and 6b are diagrams illustrating a mechanism for forming a modulated X-ray image based on an X-ray image group.
Figure 6B:
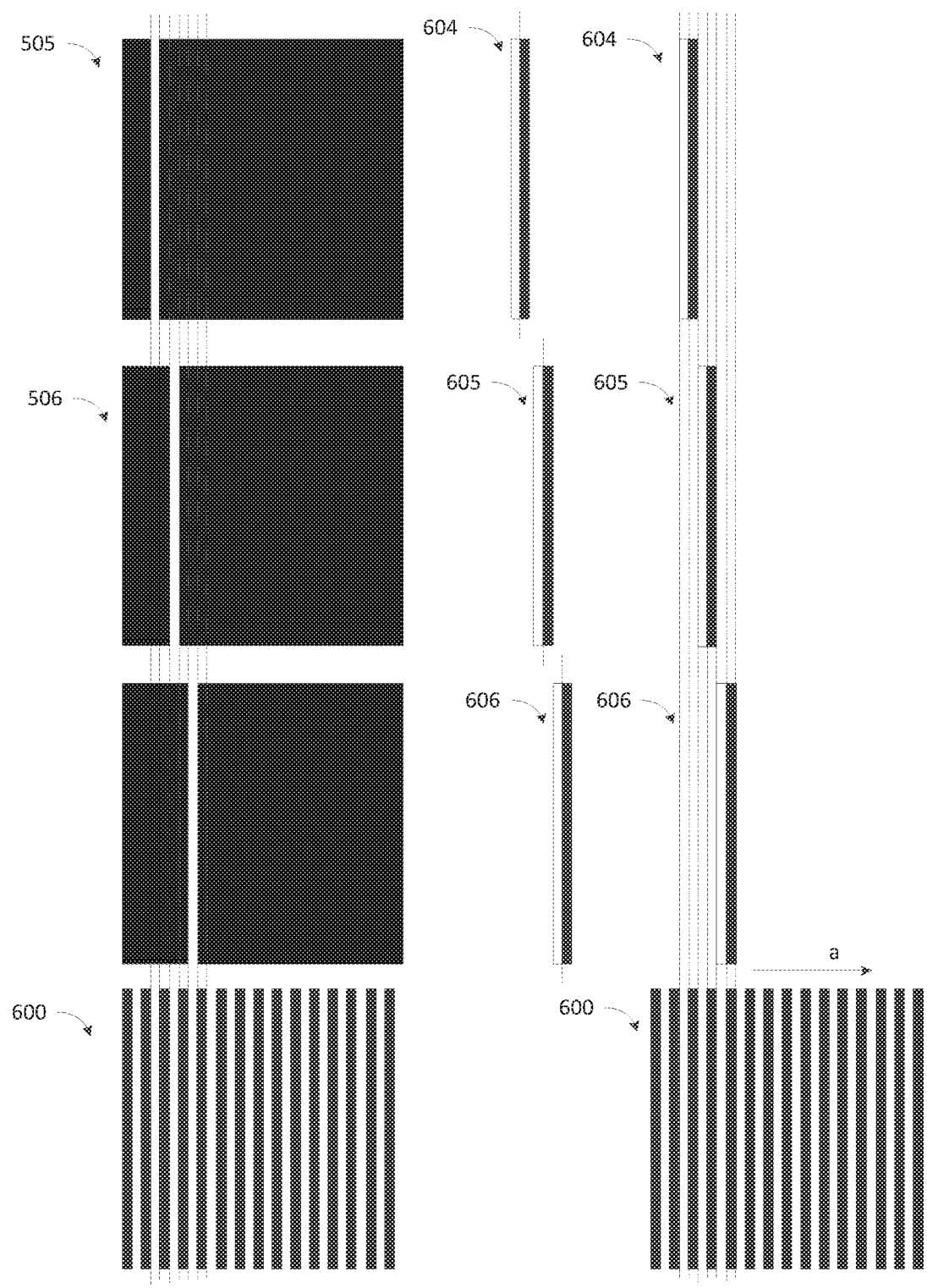

In some embodiments, as shown in FIGS. 5c and 5d, secondary collimator 201 may keep a fixed distance 205 from secondary collimator 202 in a direction "a," along which secondary collimators 201 and 202 may move together. To obtain modulated X-ray image 600, as shown in FIG. 6b, sub-zone 604, 605, etc. may be extracted from X-ray image 505, 506, etc. And sub-zones 604, 605, 606, etc. may be combined in the direction "a" and final X-ray image 600 may be obtained.

Figure 11:
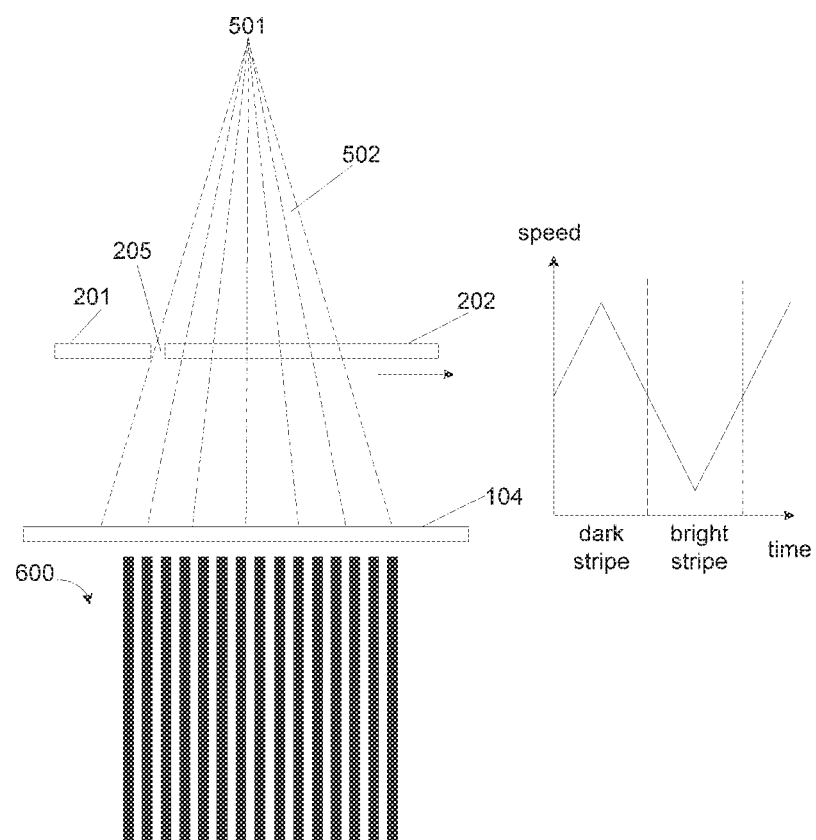
FIG. 11 is a diagram illustrating a mechanism for forming a modulated X-ray image.

In some embodiments, as shown in FIG. 11, secondary collimator 201 may keep a fixed distance 205 from secondary collimator 202 in a direction "a" along which secondary collimators 201 and 202 may move together from left to right at a periodical speed. Because the number of X-ray pulses in a unit of time may be definite, if secondary collimators 201 and 202 move slowly, the number of X-ray pulses is great on an image generated on EPID 104. If secondary collimator 201 and 202 move fast, the number of X-ray pulses is small on an image generated on EPID 104. Modulated X-ray image 600 with bright and dark stripes may be obtained by detecting the X-rays during the movement of secondary collimators 201 and 202. In some embodiments, the speed of secondary collimators 201 and 202 may be increased or decreased with a constant acceleration periodically. In some embodiments, secondary collimators 201 and 202 may move at a uniform speed with a certain ratio. For example, secondary collimators 201 and 202 may move at a speed of 3 v for a time period t, and may then move at a speed of v for a time period 3 t. Secondary collimators 201 and 202 may then move at a speed of 3 v for a time period t. Modulated X-ray image 600 may be obtained via the periodic movement.

Using a static image acquisition method, Quantum noise in a dark region may be increased compared with it in a bright region and signal-to-noise ratio may be low. In modulated X-ray image 600 obtained by detecting X-rays during movements of secondary collimators 201 and 202, the signal-to noise ratio in the dark region may be improved obviously.

Figure 7:
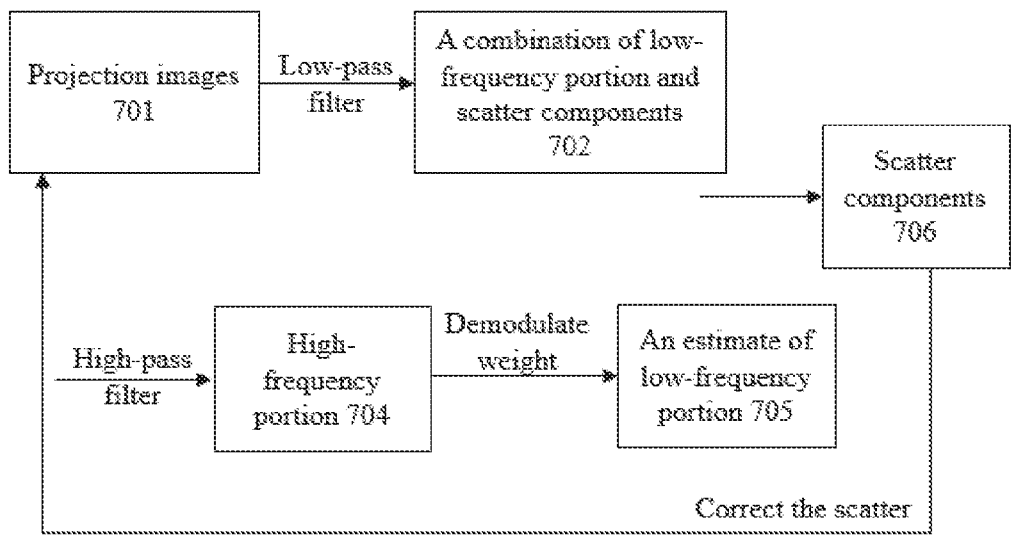
FIG. 7 is a diagram illustrating a method of eliminating scattered rays in a projection image.

The following steps S402 to S405 may be implemented with reference to the specification of patent U.S. Pat. No. 7,463,712 B2, which is incorporated herein by reference. These steps are described briefly with reference to FIG. 7.

X-ray image 600 may be processed by downsampling image 600 at a center line of every dark and bright region to avoid an influence of edge effect of secondary collimator on X-ray intensity of an image.

In S402, the modulated X-ray image may be low-pass filtered to obtain a low-frequency portion and one or more scatter components of the modulated X-ray image. The low-frequency portion and the scatter components of modulated X-ray image 600 may be obtained by low-pass filter unit 1021.

Because of characters of scatter, scatter components in modulated X-ray image 600 obtained in S401 may distribute mainly in the low-frequency portion. After projection image 701 is low-pass filtered, a combination of low-frequency portion and scatter components 702 may be obtained. In some embodiments, the projection image is a modulated X-ray image at a certain angle.

In S403, the modulated X-ray image may be high-pass filtered to obtain a high-frequency portion of the modulated X-ray image. The high-frequency portion 704 of modulated X-ray image 600 may be obtained by high-pass filter unit 1022.

Because scatter components are hardly contained in a high-frequency portion of modulated X-ray image 600, high-frequency portion 704 without scatter components may be obtained by high-pass filtering projection image 701.

In S404, the high-frequency portion may be demodulated and weighted. In addition, an estimate of the low-frequency portion of the modulated X-ray image may be obtained. The estimate of the low-frequency portion of the modulated X-ray image may be obtained by low-frequency estimate unit 1023.

High-frequency portion 704 may be demodulated and multiplied by a weight coefficient $$\frac{1-\alpha}{1+\alpha},$$

wherein $\alpha$ is a Transmission coefficient denoting an X-ray transmission of collimator. In addition, an estimate of low-frequency portion 705 may be obtained.

In S405, an estimate of the low-frequency portion of the modulated X-ray image may be subtracted from the combination of low-frequency portion and scatter components of the modulated X-ray image, and the scatter components may be obtained. The obtainment of scatter components may be performed by scatter calculation unit 1024.

Estimate of low-frequency portion 705 obtained in S404 may be subtracted from a combination of low-frequency portion and scatter components 702 obtained in S402 and an estimate of scatter components 706 may be obtained.

Figure 8:
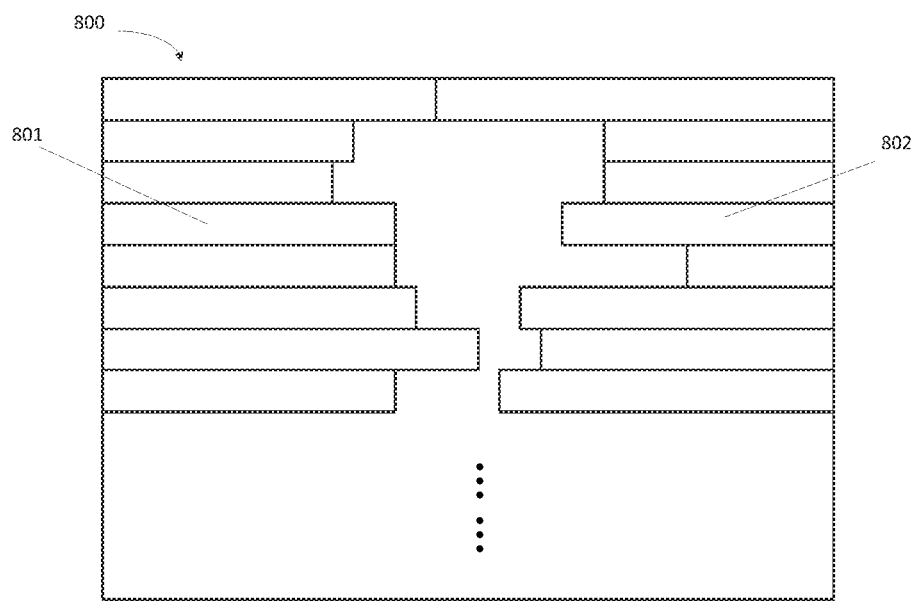
FIG. 8 is a diagram illustrating a structure of a multi-leaf collimator in an exemplary radiotherapy system.

In some embodiments, secondary collimator module 103e may be replaced by a multi-leaf collimator. As shown in FIG. 8, multi-leaf collimator 800 may include multiple pairs of leaves relatively arranged. A group of leaves 801 and another group of leaves 802 may be relatively arranged. The lengths of the leaves on one side of multi-leaf collimator 800 may be adjusted to be equal to modulate the X-rays to achieve an effect of secondary collimator module 103e.

A weight coefficient in S404 may be equal to 1 because transmittivity of multi-lead collimator 800 is almost zero when multi-leaf collimator 800 is used.

Figure 9:
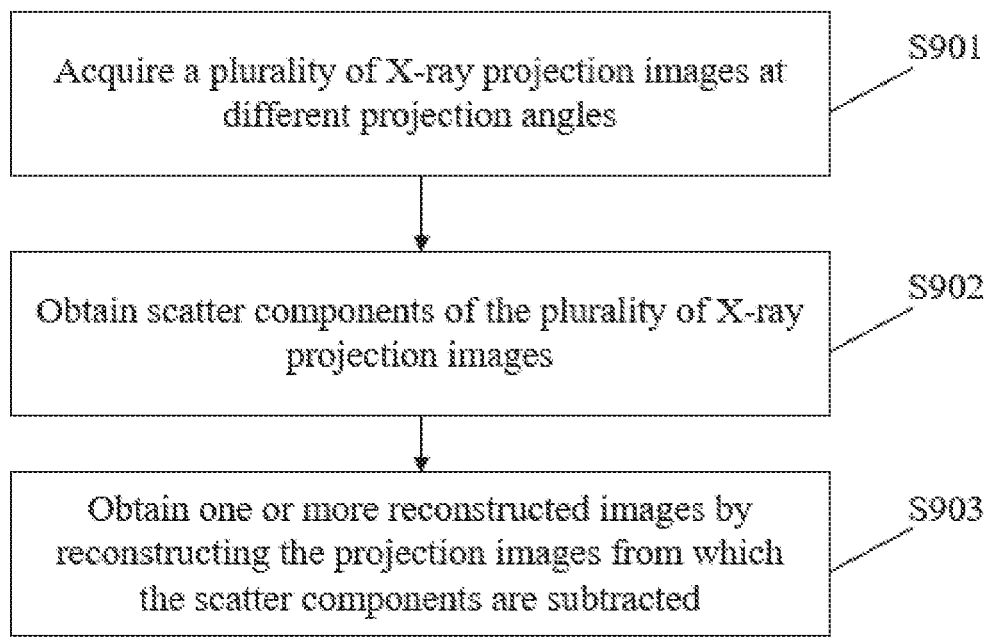
FIG. 9 is a flowchart illustrating a method of image reconstruction.

In some embodiments, a method of image reconstruction may be illustrated as follows. As shown in FIG. 9, the method may include the following steps.

In S901, a plurality of X-ray projection images from different projection angles may be acquired.

When imaging in radiotherapy system 100 as shown in FIG. 1, rotation part 102 may rotate, and treatment head 103 may output low energy X-rays. EPID 104 may acquire X-ray projection images of an imaged object at a plurality of angles. The projection images may be acquired by a common method of X-ray imaging.

In S902, scatter components of the plurality of X-ray projection images may be obtained. In some embodiments, scatter components of X-ray projection images may be obtained using the above method of calculating scatter components in X-ray images.

According to the above method of calculating scatter components in X-ray images, one or more modulated X-ray images of the imaged object may be obtained. Scatter components of the modulated X-ray images may be calculated. Because the imaged object is the same and the scatter is also the same, the scatter components calculated using the above method is equal to the scatter components in X-ray projection images obtained in S901.

In S903, one or more reconstructed images may be obtained by reconstructing the projection images from which the scatter components are subtracted.

The scatter components of projection images may be corrected by subtracting the scatter components obtained in S902 from the projection images obtained in S901. CT images of the imaged object may then be reconstructed based on the projection images. The process of image reconstruction is known to those skilled in the art and won't be described here.

Figure 10:
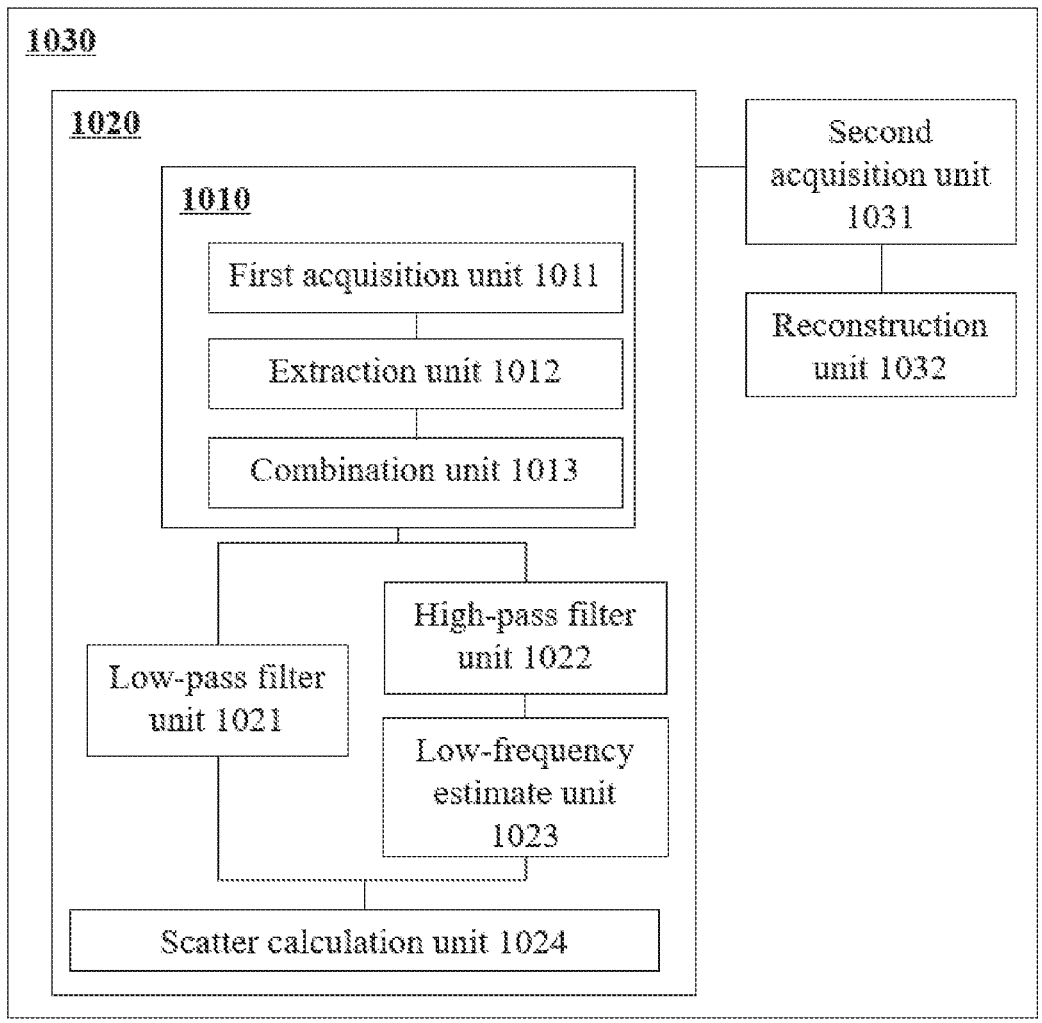
FIG. 10 is a diagram illustrating an image reconstruction apparatus.

In some embodiments, an apparatus for modulating X-ray images is provided. As shown in FIG. 10, modulated X-ray image forming apparatus 1010 may include a first acquisition unit 1011, an extraction unit 1012, and a combination unit 1013.

First acquisition unit 1011 may be configured to acquire X-rays through secondary collimator module 103e and an imaged object in sequence to generate a group of X-ray images (e.g., an X-ray image group). The acquisition may be performed during a movement of secondary collimator module 103e in a first direction. The X-ray images group may be a group of X-ray images acquired at different times of the movement of secondary collimator module 103e.

Extraction unit 1012 may be configured to extract sub-zones from the X-ray images in the X-ray image group.

Combination unit 1013 may be configured to combine the sub-zones in the first direction to form a modulated X-ray image.

In some embodiments, a device for calculating scatter components in X-ray images is provided. As shown in FIG. 10, X-ray image scatter components calculation device 1020 may include a modulated X-ray image forming equipment 1010, a low-pass filter unit 1021, a high-pass filter unit 1022, a low-frequency estimate unit 1023, and a scatter calculation unit 1024.

Modulated X-ray image forming equipment 1010 may be configured to obtain a modulated X-ray image (e.g., modulated X-ray image 600).

Low-pass filter unit 1021 may be configured to low-pass filter the modulated X-ray image to obtain a low-frequency portion and scatter components of the modulated X-ray image.

High-pass filter unit 1022 may be configured to high-pass filter the modulated X-ray image to obtain a high-frequency portion of the modulated X-ray image.

Low-frequency estimate unit 1023 may be configured to demodulate the high-frequency portion of the modulated X-ray image and weight it to obtain an estimate of the low-frequency portion of the modulated X-ray image.

Scatter calculation unit 1024 may be configured to obtain a scatter components by subtracting the estimate of the low-frequency portion of the modulated X-ray image from the low-frequency portion and scatter components of the modulated X-ray image.

In some embodiments, an apparatus of X-ray image reconstruction is provided. As shown in FIG. 10, X-ray image reconstruction apparatus 1030 may include a second acquisition unit 1031, a reconstruction unit 1032, and X-ray image scatter components calculation device 1020.

Second acquisition unit 1031 may be configured to acquire X-ray projection images of an imaged object from different projection angles.

X-ray image scatter components calculation device 1020 may be configured to calculate scatter components of the projection images.

Reconstruction unit 1032 may be configured to reconstruct images based on the projection images from which scatter components are subtracted to obtain the reconstruction images.

Modulated X-ray image forming equipment 1010, X-ray image scatter components calculation device 1020, and X-ray image reconstruction apparatus 1030 may implement the corresponding methods in the disclosure respectively.

In the present disclosure, an intensity distribution of X-rays may be adjusted flexibly using a collimator without adding any extra hardware. X-ray images with bright and dark stripes may be formed to calculate scatter components in the X-ray images. Finally, scatter in the X-ray images may be eliminated. Because secondary collimator module 103e is installed on the treatment head 103, mechanical stability may be excellent and motion blur may not be generated because of shake of geometric position.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as an "apparatus," "device," "equipment," "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the operator's computer, partly on the operator's computer, as a stand-alone software package, partly on the operator's computer and partly on a remote computer or entirely on the remote computer or server. In the latter scenario, the remote computer may be connected to the operator's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities of ingredients, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method for using in an X-ray image device, comprising:
    forming a modulated X-ray image, comprising:
    acquiring X-rays through a collimator module and an imaged object in sequence to generate an X-ray image group including a plurality of X-ray images;
    wherein the collimator module includes a pair of collimators arranged within a distance in a first direction, the acquisition is performed during a movement of the collimator module in the first direction, and the pair of collimators, during the movement of the collimator module, keep the distance and move at a periodic speed—
    extracting sub-zones from the plurality of X-ray images in the X-ray image group; and
    combining the sub-zones in the first direction to form the modulated X-ray image.

2. The method of claim 1, wherein an acquisition frequency for obtaining the X-ray image group is proportional to a speed of movement of the collimator module.

3. The method of claim 1, wherein the collimator module is a multi-leaf collimator comprising a group of leaves, and wherein the group of leaves are equal in length and move together in the first direction.

4. A method for using in an X-ray image device, comprising:
    forming a modulated X-ray image, comprising:
    acquiring X-rays through a collimator module and an imaged object in sequence to generate an X-ray image group of a plurality of X-ray images;
    wherein the acquisition is performed during a movement of the collimator module in a first direction;
    wherein the collimator module comprises a pair of collimators arranged within a distance in the first direction; and
    wherein during the movement of the collimator module, the pair of collimators keep the distance and move at a periodic speed.

5. The method of claim 4, wherein the periodic speed is at least one of a periodically increasing speed or a periodically decreasing speed.

6. The method of claim 1, further comprising:
    low-pass filtering the modulated X-ray image to obtain a combination of a low-frequency portion of the modulated X-ray image and scatter components of the modulated X-ray image;
    high-pass filtering the modulated X-ray image to obtain a high-frequency portion of the modulated X-ray image;
    calculating an estimate of the low-frequency portion of the modulated X-ray image after the high-frequency portion is demodulated and weighted; and
    calculating the scatter components by subtracting the estimate of the low-frequency portion of the modulated X-ray image from the combination of low-frequency portion and the scatter components of the low-pass filtered modulated X-ray image.

7. A method of X-ray image reconstruction, comprising;
    acquiring X-ray projection images of an imaged object from different projection angles; wherein the acquisition is performed during a movement of a collimator module in a first direction, and wherein the X-ray projection images are acquired at different times during the movement of the collimator module;
    calculating scatter components of the projection images, comprising:
    low-pass filtering a modulated X-ray image to obtain a combination of a low frequency portion of the modulated X-ray image and scatter components of the modulated X-ray image;
    high-pass filtering the modulated X-ray image to obtain a high-frequency portion of the modulated X-ray image;
    calculating an estimate of the low-frequency portion of the modulated X-ray image after the high-frequency portion is demodulated and weighted;
    calculating the scatter components by subtracting the estimate of the low-frequency portion of the modulated X-ray image from the combination of the low-frequency portion and the scatter components of the low-pass filtered modulated X-ray image; and
    obtaining at least one reconstructed image by reconstructing the projection images from which the scatter components are subtracted.

8. An apparatus, comprising:
    a first acquisition unit configured to acquire X-rays through a collimator module and an imaged object in sequence to generate an X-ray image group including a plurality of X-ray images;

wherein the collimator module includes a pair of collimators arranged within a distance in a first direction; and wherein the acquisition is performed during a movement of the collimator module in the first direction, and the pair of collimators, during the movement of the collimator module, keep the distance and move at a periodic speed;

an extraction unit configured to extract sub-zones from the X-ray images in the X-ray image group; and a combination unit configured to combine the sub-zones in the first direction to form the modulated X-ray image.

9. The apparatus of claim 8, further comprising an X-ray image scatter calculation device comprising;

a low-pass filter unit configured to low-pass filter the modulated X-ray image to obtain a combination of a low-frequency portion and scatter components of the modulated X-ray image;

a high-pass filter unit configured to high-pass filter the modulated X-ray image to obtain a high-frequency portion of the modulated X-ray image;

a low-frequency estimate unit configured to demodulate the high-frequency portion of the modulated X-ray image and weight the high-frequency portion to obtain an estimate of the low-frequency portion of the modulated X-ray image; and a scatter calculation unit configured to obtain at least one scatter component by subtracting the estimate of low-frequency portion of the modulated X-ray image from the combination of the low-frequency portion and scatter components of the modulated X-ray image.

10. The apparatus of claim 8, further comprising an X-ray image reconstruction apparatus comprising:

a second acquisition unit configured to acquire X-ray projection images of an imaged object from different projection angles:

a reconstruction unit configured to reconstruct at least one image based on the X-ray projection images from which scatter components are subtracted; and an X-ray image scatter component calculation device configured to calculate scatter components of the X-ray projection images.

11. The method of claim 4, further comprising:

low-pass filtering the modulated X-ray image to obtain a combination of a low-frequency portion of the modulated X-ray image and scatter components of the modulated X-ray image;

high-pass filtering the modulated X-ray image to obtain a high-frequency portion of the modulated X-ray image;

calculating an estimate of the low-frequency portion of the modulated X-ray image after the high-frequency portion is demodulated and weighted; and calculating the scatter components by subtracting the estimate of the low-frequency portion of the modulated X-ray image from the combination of low-frequency portion and the scatter components of the low-pass filtered modulated X-ray image.

12. The method of claim 1, wherein the periodic speed is at least one of a periodically increasing speed or a periodically decreasing speed.

13. The method of claim 4, wherein an acquisition frequency for obtaining the X-ray image group is proportional to a speed of movement of the collimator module.

14. The apparatus of claim 8, wherein the periodic speed is at least one of a periodically increasing speed or a periodically decreasing speed.

15. The apparatus of claim 8, wherein an acquisition frequency for obtaining the X-ray image group is proportional to a speed of movement of the collimator module.

16. The apparatus of claim 8, wherein the collimator module is a multi-leaf collimator comprising a group of leaves, and wherein the group of leaves are equal in length and move together in the first direction.

17. The method of claim 4, wherein the collimator module is a multi-leaf collimator comprising a group of leaves, and wherein the group of leaves are equal in length and move together in the first direction.

18. The method of claim 7, wherein the collimator module is a multi-leaf collimator comprising a group of leaves, and wherein the group of leaves are equal in length and move together in the first direction.

19. The method of claim 7, wherein the collimator module includes a pair of collimators arranged within a distance in the first direction, and wherein the pair of collimators, during the movement of the collimator module, keep the distance and move at a periodic speed.

20. The method of claim 19, wherein the periodic speed is at least one of a periodically increasing speed or a periodically decreasing speed.

* * * * *